(12) United States Patent
Borch

(10) Patent No.: US 9,162,227 B2
(45) Date of Patent: Oct. 20, 2015

(54) SAMPLE PROCESSING CARTRIDGE AND METHOD OF PROCESSING AND/OR ANALYSING A SAMPLE UNDER CENTRIFUGAL FORCE

(75) Inventor: Stig Morten Borch, Oslo (NO)

(73) Assignee: Stiftelsen Sintef, Oslo (NO)

(*) Notice: Subject to any disclaimer, the term of this patent is extended or adjusted under 35 U.S.C. 154(b) by 221 days.

(21) Appl. No.: 13/519,836

(22) PCT Filed: Dec. 28, 2010

(86) PCT No.: PCT/NO2010/000488
§ 371 (c)(1),
(2), (4) Date: Jul. 18, 2012

(87) PCT Pub. No.: WO2011/081530
PCT Pub. Date: Jul. 7, 2011

(65) Prior Publication Data
US 2012/0282707 A1    Nov. 8, 2012

(30) Foreign Application Priority Data
Dec. 29, 2009 (NO) .................................. 200933596

(51) Int. Cl.
*G01N 21/07* (2006.01)
*B01L 3/00* (2006.01)

(52) U.S. Cl.
CPC ..... *B01L 3/502738* (2013.01); *B01L 3/502753* (2013.01); *B01L 2200/0621* (2013.01);
(Continued)

(58) Field of Classification Search
CPC .......................... G01N 21/07; B01L 2300/087
USPC ....................................................... 436/177
See application file for complete search history.

(56) References Cited

U.S. PATENT DOCUMENTS

| 3,420,436 A | 1/1969 | Ito |
| 4,199,459 A | 4/1980 | Filipowicz et al. |

(Continued)

FOREIGN PATENT DOCUMENTS

| EP | 1 302 244 | 4/2003 |
| EP | 1 669 733 | 6/2006 |

(Continued)

OTHER PUBLICATIONS

Search Report dated Jul. 30, 2010, directed to Norwegian Application No. 20093596; 2 pages.

(Continued)

*Primary Examiner* — Christopher A. Hixson
*Assistant Examiner* — Emily Berkeley
(74) *Attorney, Agent, or Firm* — Morrison & Foerster LLP

(57) ABSTRACT

A sample processing cartridge for carrying out processing under centrifugal force acting in at least two directions as the orientation of cartridge relative to centrifugal force is changed, the cartridge comprising: a first cavity adapted to contain a sample; and a second cavity in fluid communication with the first cavity, wherein the first and second cavities are arranged such that the sample in the first cavity is moved therefrom to the second cavity as a centrifugal force acting on the cartridge is changed from a first direction to a second direction, the first cavity is elongated perpendicular to the centrifugal force acting in the first direction, and the second cavity is more shallow than the first cavity and more extended in the direction of the centrifugal force acting in the second direction than the first cavity is extended in the direction of the centrifugal force acting in the first direction.

12 Claims, 9 Drawing Sheets

(52) U.S. Cl.
CPC .. *B01L2300/0681* (2013.01); *B01L 2300/0806* (2013.01); *B01L 2300/087* (2013.01); *B01L 2300/0874* (2013.01); *B01L 2300/0887* (2013.01); *B01L 2400/0409* (2013.01); *B01L 2400/0622* (2013.01); *B01L 2400/0688* (2013.01); *G01N 21/07* (2013.01); *Y10T 436/25375* (2015.01)

(56) References Cited

U.S. PATENT DOCUMENTS

| | | | |
|---|---|---|---|
| 4,814,282 | A | 3/1989 | Holen et al. |
| 4,883,763 | A * | 11/1989 | Holen et al. ............ 436/45 |
| 6,593,143 | B1 | 7/2003 | Gordon |
| 7,688,449 | B2 | 3/2010 | Ogawa et al. |
| 2006/0083667 | A1 | 4/2006 | Kohara et al. |
| 2007/0243111 | A1 | 10/2007 | Momose |
| 2007/0262034 | A1 | 11/2007 | Ducree et al. |
| 2009/0142232 | A1 * | 6/2009 | Okada et al. ............ 422/72 |
| 2009/0209752 | A1 * | 8/2009 | Peters et al. ............ 536/25.41 |
| 2009/0269854 | A1 | 10/2009 | Kageyama |
| 2010/0132820 | A1 | 6/2010 | Ozaki et al. |
| 2012/0301972 | A1 | 11/2012 | Borch |

FOREIGN PATENT DOCUMENTS

| | | | | |
|---|---|---|---|---|
| EP | 1669733 A1 * | 6/2006 | ............ | G01N 1/10 |
| EP | 1 873 529 | 1/2008 | | |
| JP | 2001-353451 | 12/2001 | | |
| WO | WO-03/083491 | 10/2003 | | |
| WO | WO 03083491 A2 * | 10/2003 | ............ | G01N 35/00 |
| WO | WO-2005/033666 | 4/2005 | | |
| WO | WO-2007/090620 | 8/2007 | | |
| WO | WO-2008/139697 | 11/2008 | | |
| WO | WO-2009/085884 | 7/2009 | | |

OTHER PUBLICATIONS

Search Report and Written Opinion mailed Apr. 27, 2011, directed to International Patent Application No. PCT/NO2010/000489; 12 pages.

International Search Report and Written Opinion mailed May 6, 2011, directed to International Application No. PCT/NO2010/000488; 10 pages.

International Preliminary Report on Patentability dated Apr. 10, 2012, directed to International Application No. PCT/NO2010/000488; 13 pages.

Notice of Reasons for Rejection mailed Aug. 4, 2014, directed to JP Application No. 2012-547047; 3 pages.

Notice of Reasons for Rejection mailed Mar. 30, 2015, directed to JP Application No. 2012-547047; 3 pages.

* cited by examiner

SAMPLE PROCESSING CARTRIDGE AND METHOD OF PROCESSING AND/OR ANALYSING A SAMPLE UNDER CENTRIFUGAL FORCE

CROSS-REFERENCE TO RELATED APPLICATIONS

This application is a national stage application under 35 USC 371 of International Application No. PCT/NO2010/000488, filed Dec. 28, 2010, which claims the priority of Norway Patent Application No. 20093596, filed Dec. 29, 2009, the contents of which prior applications are incorporated herein by reference.

FIELD OF THE INVENTION

The present invention relates to a sample processing cartridge or container. The present invention also relates to a method of processing and/or analysing a sample under centrifugal force.

BACKGROUND OF THE INVENTION

Centrifugation as a mean for accelerating sedimentation of cells, particles and precipitates as well as for separation of liquids or cells with different density has long been an integral part of chemical and biochemical protocols.

Two-dimensional centrifugation is generally obtained in an apparatus that performs rotation of the individual cartridges around one axis, while these cartridges are being rotated by separate means around another distal axis.

U.S. Pat. No. 4,883,763 (Holen et al.) discloses a sample processor card formed of a substantially closed chamber which includes a supply of reagent therein. The card includes inlet means for supplying a sample to the card, capillary means communicating with the inlet means to receive a sample supplied to the card and overflow means communicating with the capillary means to receive excess sample which is advanced from the inlet means through the capillary means under the influence of centrifugal force applied to the card in a first direction. The card also includes holding chamber means adapted to receive reagent from the reagent supply and sample from the capillary means in response to centrifugal force acting on the card in a second direction, and cuvette means communicating with the holding chamber means which is adapted to permit the measurement of the chemical reaction between the reagent and the sample. By use of the sample processor card, flow of the reagent and the sample within the card is supposedly achieved solely by centrifugal force acting in two or more directions on the card as the card is subjected to high centrifugal forces in a centrifuge.

SUMMARY OF THE INVENTION

It is an object of the present invention to provide an improved sample processing cartridge and method.

This object, and other objects that will be apparent from the following description, is achieved by the present invention as defined in the appended independent claim(s). Further embodiments are set forth in the appended dependent claims.

According to an aspect of the present invention, there is provided a sample processing cartridge for carrying out processing under centrifugal force acting in at least two directions as the orientation of cartridge relative to centrifugal force is changed, the cartridge comprising: a first cavity adapted to contain a sample; and a second cavity in fluid communication with the first cavity, wherein the first and second cavities are arranged such that the sample in the first cavity is moved therefrom to the second cavity as a centrifugal force acting on the cartridge is changed from a first direction to a second direction, (a) the first cavity is elongated (in a plane of the cartridge) perpendicular to the centrifugal force acting in the first direction, and (b) the second cavity is more shallow than the first cavity and more extended in the direction of the centrifugal force acting in the second direction than the first cavity is extended in the direction of the centrifugal force acting in the first direction.

A technical effect resulting from (a) is that material with higher density than the rest of the sample in each point of the elongated sample has a shorter way to the "bottom" of the first cavity. A technical effect resulting from (b) is that the sample in the shallower second cavity gets more spread out in the direction of the centrifugal force, which facilitates the removal of e.g. plasma from the sample. Overall, the cartridge allows for very fast and accurate microseparation of fluidic elements (e.g. plasma from cells or nano-/micro-particles from liquid) of different density, when exposed to sufficient centrifugal forces. It allows for the separation not only of particles (including cells) from liquids, but also separation of liquids of different density (e.g. lipids from plasma), or the separation of particles (including cells) of different density.

In said plane, or in a plane parallel to said plane, the second cavity may be less extended perpendicular to the centrifugal force acting in the second direction than the first cavity is elongated perpendicular to the centrifugal force acting in the first direction.

The cartridge may further comprise at least one of an overlying layer and an underlying layer with at least one additional cavity and/or channel to which the sample or material originating therefrom may be moved. This allows for processing or testing or analysis in three dimensions. The liquid may be moved back and forth between multiple layers providing increased functionalities in a compact cartridge.

The cartridge may further comprise a substantially V- or U-shaped micro channel for metering the sample or material originating therefrom. By subjecting the cartridge to a centrifugal force exceeding the capillary force of the V- or U-shaped microchannel, the meniscuses of a liquid in the V- or U-shaped microchannel may always be perfectly perpendicular to the centrifugal force, thereby improving the accuracy of the liquid volume contained in the metering channel of the cartridge.

The cartridge may further comprise at least one trap adapted to stop higher density fluidic particles but to let pass lower density liquids and/or fluidic particles. A trap serving as an example includes an inlet chamber, an intermediate U-shaped channel, an outlet chamber, a first two-channel splitter between the inlet chamber and one end of the intermediate channel, and a second two-channel splitter between the opposite end of the intermediate channel and the outlet chamber. Another trap serving as an example includes a kidney-shaped loop with inlet and outlet at the concave portion thereof. By these traps, there is no need to include porous barriers for retaining the particles. Further, the lower density fluidic particles may efficiently and repeatedly pass the higher density fluidic particles, and interact therewith.

Further, the first cavity may be elongated in a plane of the cartridge and have a depth perpendicular to said plane, wherein the second cavity has a smaller depth than the first cavity and extends in said plane in a different direction and by a greater amount than the width of the first cavity.

Further, the second cavity may be configured as a channel system.

Further, the cartridge may comprise at least one porous material arranged in a cavity or channel of the cartridge, such that other material (e.g. the sample or material originating therefrom and/or at least one reagent or similar) may pass (transversal and/or lateral flow) through the porous material by changing the orientation of the cartridge relative to the centrifugal force. For example, the porous material may be arranged in an inter-level channel to the overlying layer and/or an underlying layer. Also, the cartridge may comprise an inlet to the inter-level channel, which inlet is provided at one end of the inter-level channel in one layer of the cartridge, wherein the inlet is arranged in substantially the same direction as an outlet from the inter-level channel, which outlet is provided at the other end of the inter-level channel in another layer of the cartridge, making the liquid flow through the entire volume of the inter-level channel. The porous material may for instance be a filter, a porous membrane, a crossflow filter, channels or cavities with pillars, one or more porous stoppers for holding beads or particulate material, channels filled with particulate or fibrous materials or spherical beads, etc. The filter or porous membrane may be positioned in any angle between 0 degrees to 90 degrees to the plane of a disc-shaped cartridge. The porous material may function as size filters for retaining molecules and particles of different molecular weights as used for concentration, separation and fractionation or medium exchange purposes, but also based upon chemical and/or electrochemical characteristics. Further, the porous material may also be any type of sensors, reactors or actuators through which fluid/liquid flow, typically a photonic crystal sensor. Further, surfaces of said porous material may be chemically functionalized with positively or negatively charged groups, polar groups, hydrophobic groups or chemical groups with other types of chemical features or activities that may interact with molecules within the fluid. Typically these may be various types of chromatographic media, such as silica, ion exchange materials and so on. Further, the surfaces of said porous material may be chemically functionalized with molecules with specific capturing features, chemical activities such as enzymes or other types of catalytic materials. These molecules may be specific antibodies, nucleic acid probes, lectines or any one element of a receptor ligand system, for example (Strept)avidin and biotin, an enzyme and its enzyme substrate. The combination of liquid flow, as controlled by the orientation of the cartridge relative to the centrifugal force, through porous materials exposing a large surface area to volume ratio allow for extensive interactions between molecules in solution and reactive groups on the surface of the porous materials and will thereby significantly increase the speed of any chemical or physical reaction such as binding, capturing, enzymatic transfer etc. The changed orientation of the cartridge relative to the centrifugal force may be used to flush the liquid back and forth through the porous material, actuator, reactor or sensor and thereby increasing the probability of molecules in solution to interact with immobilized groups on the surface of the porous material.

According to another aspect of the present invention, there is provided a method of processing and/or analysing a sample under centrifugal force, the method comprising: providing the sample in the first cavity of a sample processing cartridge as described above; subjecting the cartridge to a centrifugal force acting in the first direction; and changing the centrifugal force from the first direction to the second direction. This aspect may exhibit similar features and technical effects as the previously described aspect.

The cartridge may be subjected to the centrifugal force by rotating the cartridge about an external axis, wherein the direction of the centrifugal force is changed by rotating the cartridge about an axis within the cartridge.

Further, the cartridge may be subjected to a centrifugal force exceeding the capillary force of the (above-mentioned) V- or U-shaped micro channel.

Further, the sample or material originating therefrom may be allowed to enter a (second) system of channels and cavities that are extending laterally in a plane of the cartridge parallel to a first system of channels and cavities including said first and second cavity.

The method may further comprise: changing the orientation of the cartridge relative to the centrifugal force such the other material fluid passes through the (above-mentioned) porous material.

According to the present invention, there is also provided a sample processing cartridge for carrying out processing or the like under centrifugal force acting in at least two directions, the cartridge comprising: a first cavity adapted to contain a sample; and a second cavity or channel system in fluid communication with the first cavity, wherein the first cavity is elongated in a plane of the cartridge and has a depth perpendicular to said plane, and wherein the second cavity or channel system has a smaller depth than the first cavity and extends in said plane (or in a plane parallel to said plane) in a different direction and by a greater amount than the width of the first cavity. This cartridge may exhibit similar features and technical effects as the previously described aspects. In particular, it allows for very fast micro separation of fluidic elements (e.g. plasma from cells or nano-/micro-particles from liquid) of different density.

BRIEF DESCRIPTION OF THE DRAWINGS

These aspects and more of the present invention will now be described in further detail, with reference to the appended drawings showing embodiments of the invention.

DETAILED DESCRIPTION OF THE INVENTION

Figure 1A:
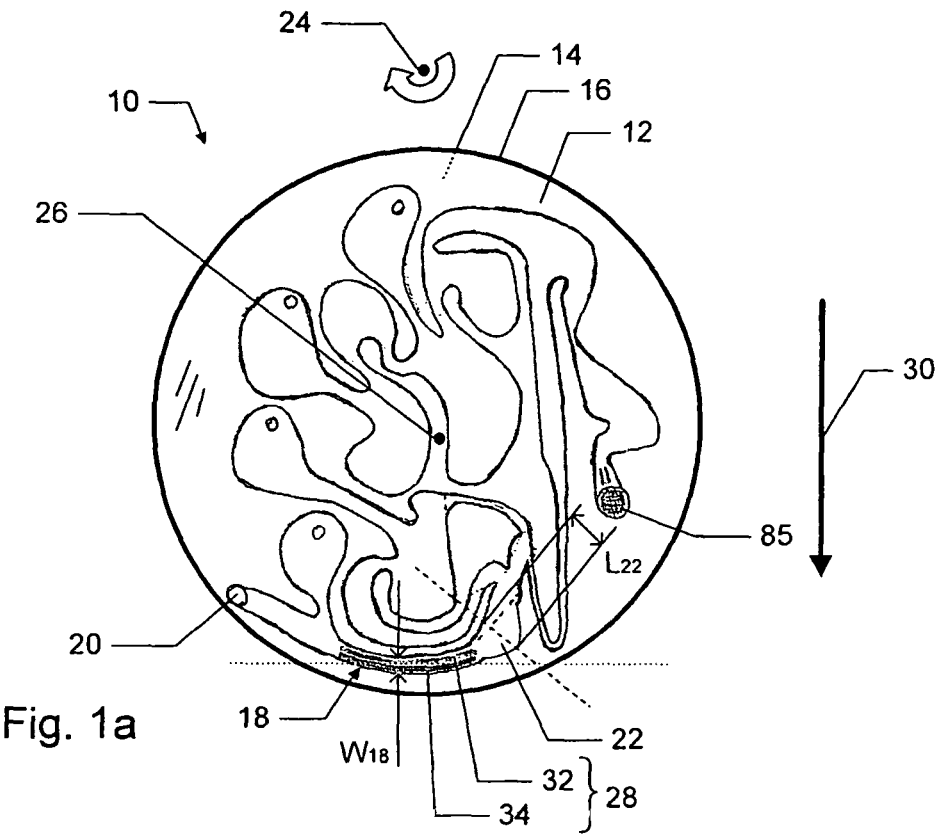
FIGS. 1a-1c are top views of a sample processing cartridge according an embodiment of the invention.

Generally, the present invention seeks to provide analytical sample and reagent processing devices (cartridges) and methods, wherein the devices can be provided with stored reagents therein, and in which chemical assay sequences can be carried out in two or three dimensions by supplying a sample thereto and then applying centrifugal forces acting in two or more directions thereto by changing the orientation of the cartridge relative to the centrifugal force in a controlled way, to effectively transfer liquids from one cavity or chamber therein to one or more others chambers (splitting), mixing reagents and sample, and allowing effective interaction between soluble reactants and functionalized surfaces and measure a chemical response.

The present invention further seeks to provide novel fluidic functionalities that both can be used for efficient separation of fluidic elements (liquids, cells, dissolved nano- and microparticles, fibres and debris of such) of different density as well as processing and transporting both nL-quantities, µL-quantities as well as mL-quantities of various liquids within micro channels and cavities of a variety of shapes within the cartridge and forcing these liquids to interact with very large functionalized surfaces such as obtained in channels or cavities holding nano- and/or micro-particles, porous structures (e.g. porous membrane and/or filters) and pillar structures. The functionalities do not require any actuators like pumps, valves or surface modification to control the flow within the cartridge and do not need to rely upon capillary forces for directed liquid flow. This may be obtained by solely changing the orientation of the cartridge (microfluidic device) relative to the centrifugal force acting on the flowing elements in the cartridge and inventive design of cavities and microchannels in which the fluidic elements are allowed to flow.

A sample processing container or cartridge 10 according to an embodiment of the present invention will now be described with reference to FIGS. 1a-1c and 2.

The cartridge 10 includes an upper face 12 and a lower face 14, which together with side walls 16 define a generally plate or disc-shaped body. The upper and lower faces 12, 14 may be foil covers. In the body of the cartridge, there are provided a plurality of interconnected chambers or cavities and channels, etc. covered by the upper and lower faces 12, 14. The cartridge may be optically transparent or translucent. The cartridge may for instance be made of plastics, such as Cyclic Olefin Copolymer (COC), polystyrene, or polycarbonate. The cartridge may be disposable and sealable. Further, the cavities and channels of the cartridge may be provided by moulding, hot embossing, milling, etc.

In particular, the cartridge 10 comprises a first separation cavity 18. The first cavity 18 is elongated (along the dotted line in FIG. 1a) in a plane P of the cartridge parallel to the faces 12 and 14. The width of the first cavity 18 is indicated by $W_{18}$, and the length of the first cavity is indicated by $L_{18}$. Further, the cartridge comprises or is in fluid communication with an inlet means 20 for supplying a sample into the first cavity 18.

The first cavity 18 is in fluid communication with a second cavity 22 of the cartridge 10. In the embodiment shown in FIGS. 1a-1c and 2, the first and second cavities 18 and 22 are basically different portions of one cavity, but they may alternatively be separate and connected for instance by a channel (not shown).

The second cavity 22 extends in a direction (indicated by the dashed line in FIGS. 1a and 1b) in said plane parallel to the faces 12 and 14 by a measure $L_{22}$, which measure or length $L_{22}>W_{18}$. This direction is different than that of the width of the first cavity, as seen from the top view of FIGS. 1a-1c. Further, the second cavity 22 is generally less wide ($W_{22}$) than what the first cavity 18 is long ($L_{18}$). Also, the second cavity 22 is shallower than the (deeper) first cavity 18, as seen from the side view of FIG. 2. The depth of the first cavity 18 is denoted $D_{18}$, and depth of the second cavity 22 is denoted $D_{22}$. The actual difference in depth may for instance be from 2:1 to 10:1. The transition between the first cavity 18 and the second cavity 22 may be somewhat rounded or inclined.

During use, the cartridge 10 is generally horizontally arranged, and provided in a centrifuge apparatus (not shown). An example of a centrifuge apparatus that may be used in disclosed in the applicant's co-pending patent application entitled "Centrifugation apparatus, use of such an apparatus, and centrifugation method", the content of which herein is incorporated by reference. Another example of a centrifuge apparatus that could be used is disclosed in the U.S. Pat. No. 4,814,282 (Holen et al.), the content of which herein is incorporated by reference.

In the centrifuge apparatus, the cartridge 10 may be rotated about a distal vertical axis 24, for subjecting the cartridge 10 and any sample or reagent(s) therein for a centrifugal force. Further, the cartridge 10 may also be rotated about a vertical axis 26 intersecting the cartridge, so as to change the orientation of the cartridge relative to the centrifugal force. This may be denoted two-dimensional centrifugation.

In an example of a method of processing or analysing a sample under centrifugal force, a sample 28 is first provided in the first cavity 18 via the inlet means 20. The sample 28 may for instance be a blood sample, and it is typically about 10 µL (microliter), but may in principle range from a fraction of a microliter to several mL.

The cartridge is then subjected to a centrifugal force 30, typically between 100×G and 2000×G (where G is the gravitation force at Earth's surface). The centrifugal force 30 acts in a direction which is substantially perpendicular to the first cavity 18 (the first cavity 18 is elongated perpendicular to the centrifugal force 30), as seen from the view of FIG. 1a. In this step, the plasma 32 in the blood sample 28, which plasma has lower density than blood cells 34 in the blood sample 26, is separated from the heavier blood cells 34.

Then, while spinning around the axis 24, the cartridge 10 is also rotated about the internal axis 26 so that the direction of the centrifugal force relative to the microchannels and cavities of the cartridge is changed. The "new" direction of the centrifugal force acting on the cartridge is denoted 36 and illustrated in FIG. 1b. As the cartridge is so rotated, the sample is transferred from the deeper first cavity 18 to the shallower second cavity 22. Further, the second cavity 22 is more elongated in the direction of the "new" centrifugal force 36 than the first cavity was extended in the direction of the previous centrifugal force 30. That is, the length $L_{22}$ of the second cavity 22 is greater than the width $W_{18}$ of the first cavity 18.

Figure 1B:
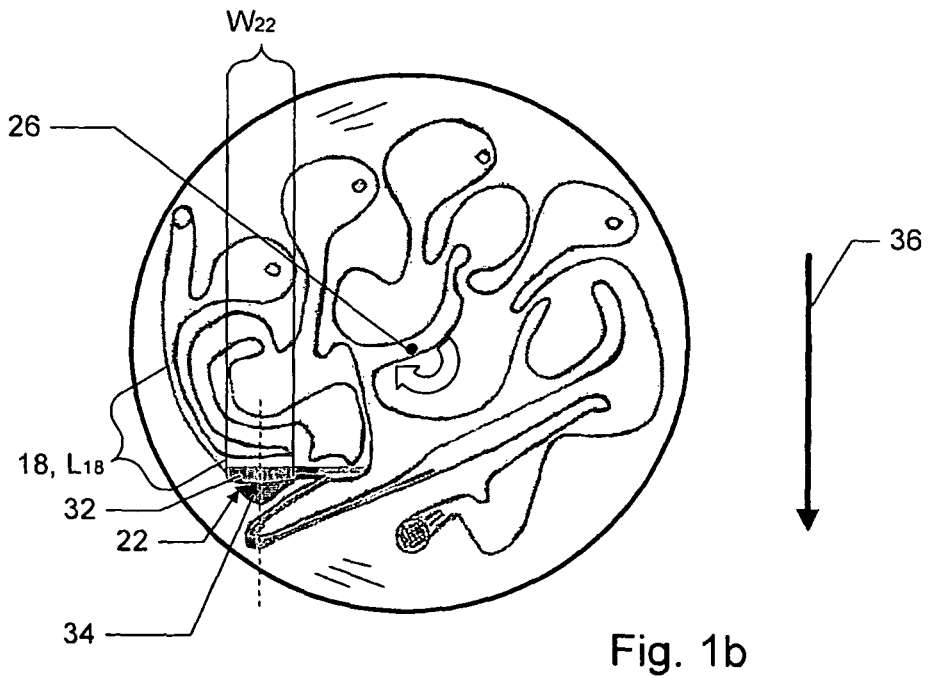
Figure 2:
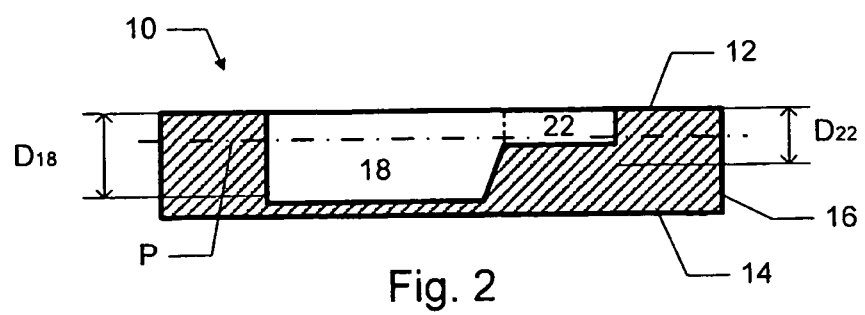
FIG. 2 is a schematic, cross-sectional side view of the cartridge in FIGS. 1a-1c.

In the shallower second cavity 22, while being subjected to the centrifugal force 36, the separated sample gets more spread out in the direction of the centrifugal force. This facilitates removing the plasma 32 by further rotating the cartridge 10 about the internal axis 26, as also illustrated in FIG. 1b, and the total time for separation is reduced. The separated plasma 32 may then be subjected to further processing or analysis or tests in other parts of the cartridge 10.

Figure 1C:
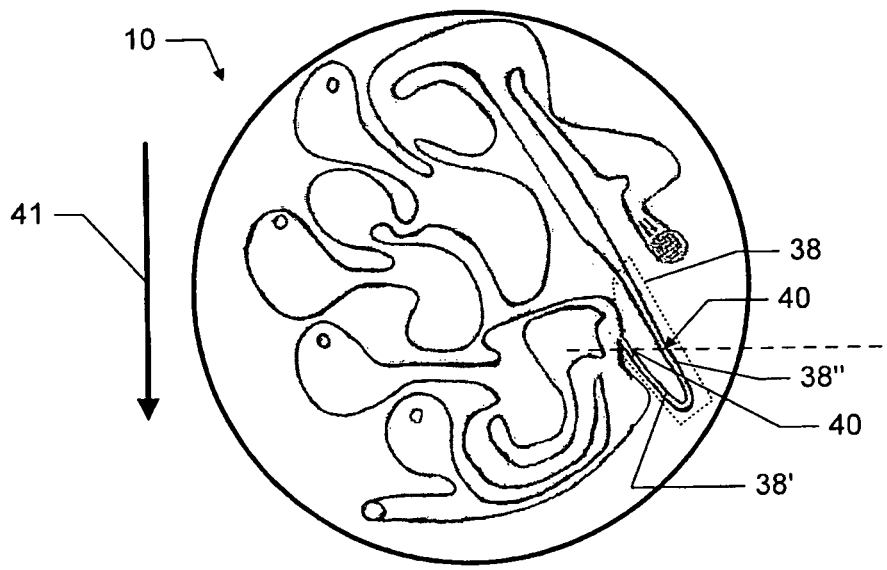

The cartridge 10 may further comprise a V- or U-shaped microchannel 38, see for instance FIG. 1c. This channel may have a variety of shapes. In order to obtain precise metering, there should be a defined microfluidic loop between the two interconnected tubes 38a, 38b, between which the liquid will equilibrate (go to same level) due to the centrifugation. The U-shaped (or V-shaped) microchannel 38 typically lies in a plane parallel to the faces 12 and 14, such as the plane P. The U-shaped microchannel 38 is typically about 50-200 µm wide. The U-shaped microchannel 38 may be arranged following the second cavity 22, for receiving and metering e.g.

plasma 32 therefrom, but it could alternatively be placed elsewhere in the cartridge 10 for other measuring purposes.

The centrifugal force continuously acting on a liquid (e.g. plasma 32) in the U-shaped microchannel 38 may be modulated to far exceed the capillary force of the micro-channel 38 at any time. For a 100 μm wide U-shaped microchannel 38, the centrifugal force for exceeding the capillary force would typically be about 100×G. When the surface tension and the capillary force is exceeded, and the curved part of the U-shape points substantially in the direction of the centrifugal force, the meniscuses 40 of the liquid will be perfectly perpendicular to the centrifugal force 41 acting on the liquid. This will improve the accuracy when measuring the liquid volume contained in the cartridge. By further rotating the cartridge relative to the centrifugal force (i.e. about the internal axis 26), the meniscuses 40 are kept perpendicular to the centrifugal force, allowing precise and controlled decanting of the liquid.

A sample processing cartridge like the cartridge 10 may further comprise at least one trap for holding higher density fluidic particles (typically particles and cells), while lower density fluid elements (liquids and particles in suspension) will be displaced by the elements of higher density and the elements of lower density are hence allowed to pass through and exit the trap according to the principle of decantation. The g-force (centrifugal force) acting on the cartridge may be varied to modulate sedimentation according to the density of the fluidic elements involved. The at least one trap may be used to isolate and wash aggregates as typically obtained through immunoaggregation (typically latex immunoassays) and/or establish columns as made of functionalized micro- or nano-particles acting as the solid phase for capturing or other types of surface related chemical or physical interactions. By means of the at least one trap, there is no need to include porous barriers retaining the particles of higher density than the liquid. The particles may be dispensed suitably anywhere within the cartridge and then the suspension may be transported through two-dimensional centrifugation into the at least one trap where a particle "column" or a porous plug is formed due to the density of the particles and the design of the cavities and channels limiting the flow of the liquid relative to the direction of centrifugal force acting on the cartridge.

Liquids, of lower density than the particles of the porous column/plug, may then by two-dimensional centrifugal actions be forced to pass quickly one or multiple times through the porous column/plug. Provided these particles are carrying chemically functional groups such as positively or negatively charged groups, polar groups, hydrophobic groups or chemical groups with other types of chemical features or activities that may interact with molecules within the fluid, immobilized biomolecules, typically enzymes or biospecific capturing molecules such as monoclonal antibodies or fragments thereof, Streptavidin, single stranded nucleic acid (N.A.) fragments/probes or other receptor molecules, the appurtenant enzyme substrates, antigens, epitopes, Avidin-carrying molecules, nucleic acid single strands or ligands in solution will be forced to interact with the immobilized receptor molecules. By this means, very fast and efficient interactions and capturing to the particles of all types of ligand molecules may be obtained as well as very efficient separation of a liquid of lower density from particles of higher density as typically utilized in washing processes. This will typically be suited for chromatographic processes where the fluidic flow at any time is carefully controlled by the direction of the centrifugal force. These types of trap designs do also improve and simplify very precise separation of liquids and/ or particles of different density according to the decantation as described in relation to FIG. 1.

An example of a trap is illustrated in FIGS. 3a-3e and denoted 42. The trap 42 includes an inlet chamber 44, an intermediate U-shaped channel 46, an outlet chamber 48, a first two-channel splitter 50 between the inlet chamber 44 and one end 52 of the intermediate channel 46, and a second two-channel splitter 54 between the opposite end 56 of the intermediate channel 46 and the outlet chamber 48. The trap 42 is typically arranged lying in a plane of the cartridge 10 parallel to the faces 12 and 14, such as the plane P.

Figure 3A:
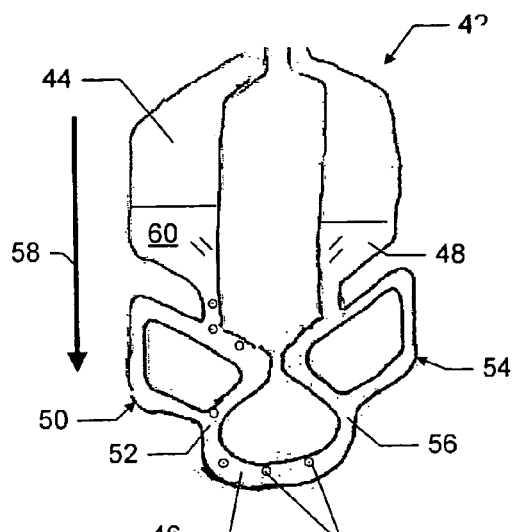
FIGS. 3a-3e are a top views of a trap according to an embodiment of the invention.

During operation or use, the trap 42 in the cartridge is first exposed to a centrifugal force 58 as illustrated in FIG. 3a. A suspension including liquid 60 and particles 62 arriving in the inlet chamber 44 is spread throughout the trap 42 due to the centrifugal force 58.

Figure 3B:
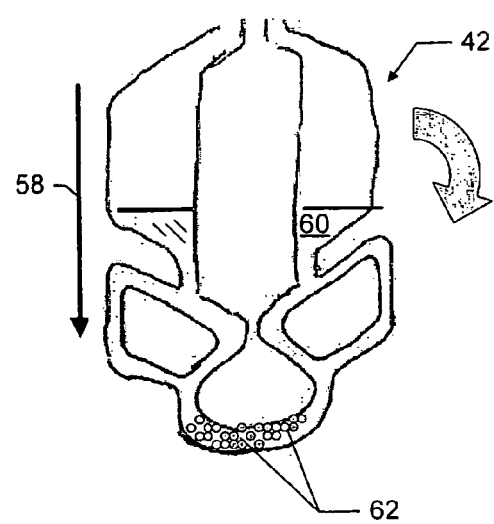

The particles 62 of the suspension will start to sediment in the U-shaped channel 46 due to the higher density than the surrounding liquid 60, and the centrifugal force 58 will eventually accomplish packaging of the particles 62 to a porous plug or column, as illustrated in FIG. 3b.

Figure 3C:
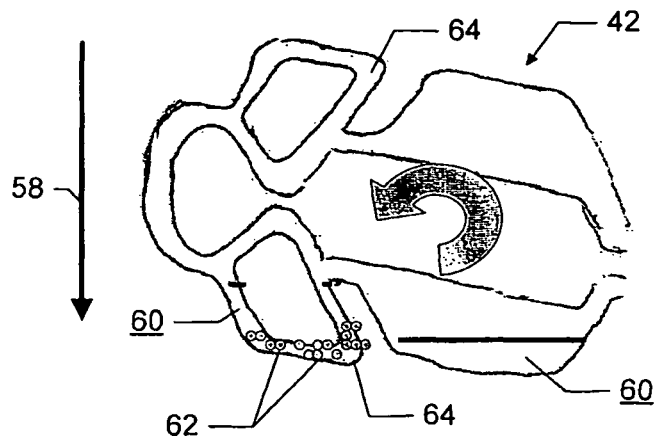
Figure 3D:
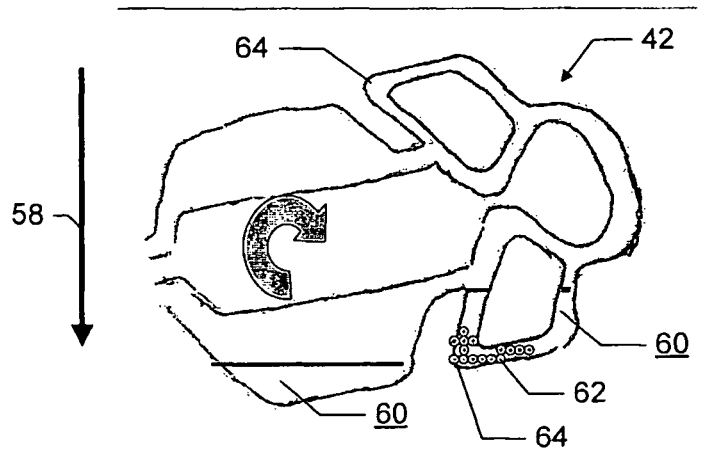

Tilting the trap 42 as indicated by the curved arrow in FIG. 3b (e.g. by rotating the cartridge around the internal axis while being rotated about the external axis) will effectively flush the liquid 60 through the column formed by the particles 62. The liquid 60 and particles 62 may at any time be moved according to the current centrifugal force, but the particles 62 of higher density than the liquid 60 will occupy the portions of the trap 42 most far away from the centrifugal centre, as further illustrated in FIGS. 3c and 3d. As seen in FIGS. 3c and 3d, the two-channel splitters 50 and 54 each has a bend 64 with an acute angle (<90 degrees) for trapping the particles 62, while the liquid 60 may pass.

Repeated controlled tilting of the cartridge (and hence of the trap 42) may retain the particles 62 within the trap 42, while the liquid 60 flows back and forth through the plug or column formed by the particles 62, forcing molecules in the liquid 60 to interact with surface molecules of the particles 62. This allows for efficient interactions in a variety of receptor ligand systems as well as efficient washing.

Figure 3E:
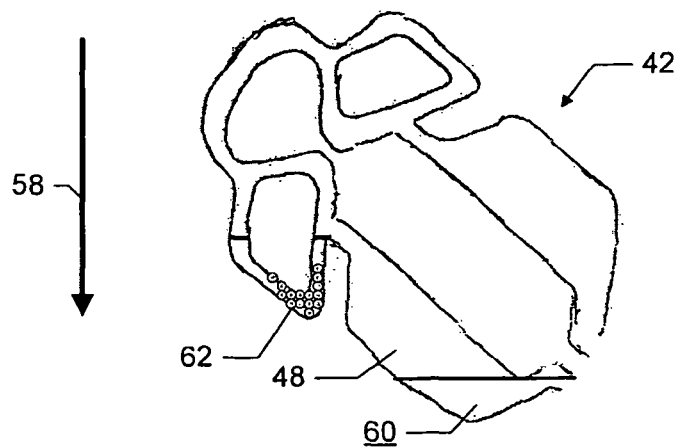

A majority of the liquid 60 may be separated from the particles 62, except a small fraction surrounding the particles 62 (void volume), and emptied from the trap 42 via an output of the outlet chamber 48 as illustrated in FIG. 3e.

Figure 4:
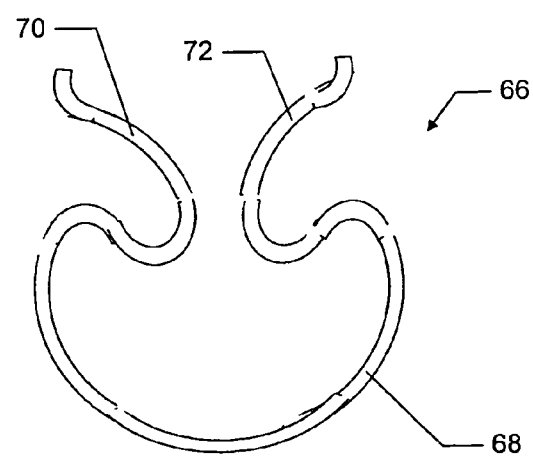
FIG. 4 is a top view of a trap according to another embodiment of the invention.

Another example of a trap is illustrated in FIG. 4 and denoted 66. The trap 66 includes a kidney-shaped loop channel 68 with an inlet 70 and an outlet 72 at the concave portion thereof. The trap 66 is typically arranged lying in a plane of the cartridge 10 parallel to the faces 12 and 14 (e.g. plane P), and the function of the trap 66 is similar to that of the trap 42 illustrated in FIGS. 3a-3e.

Combinations of the designs in FIG. 3 and FIG. 4 and variants thereof may be designed according to the process and materials involved in the assay.

Figure 5:
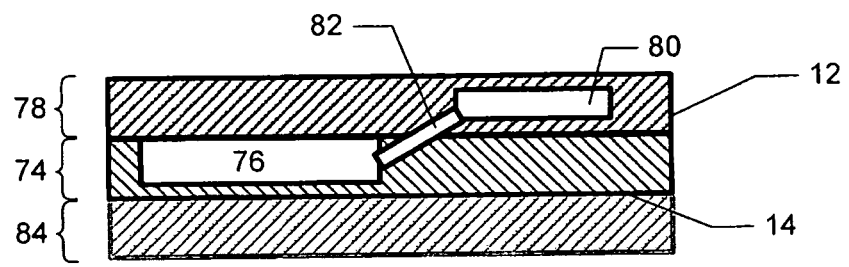
FIG. 5 is a schematic, cross-sectional side view of a sample processing cartridge according to an embodiment of the invention.
Figure 8:
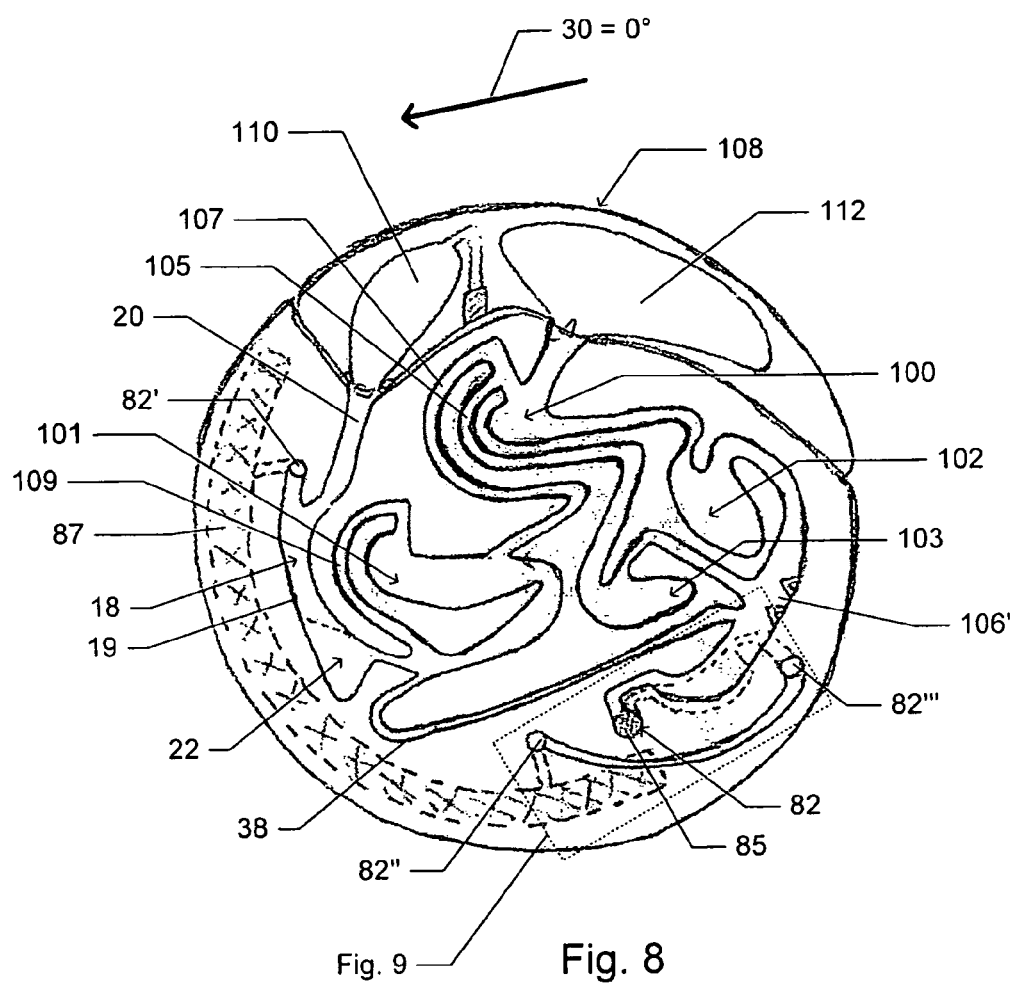
FIG. 8 is a top view of yet another sample processing cartridge according to an embodiment or embodiments of the invention.
Figure 9:
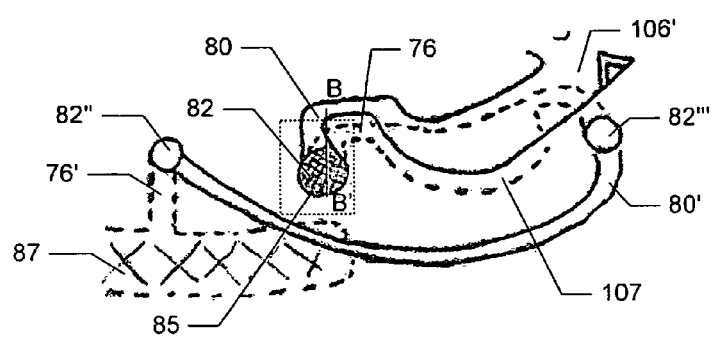
FIG. 9 is an enlarged top view showing a porous filter membrane in the cartridge of FIG. 8.
Figure 10:
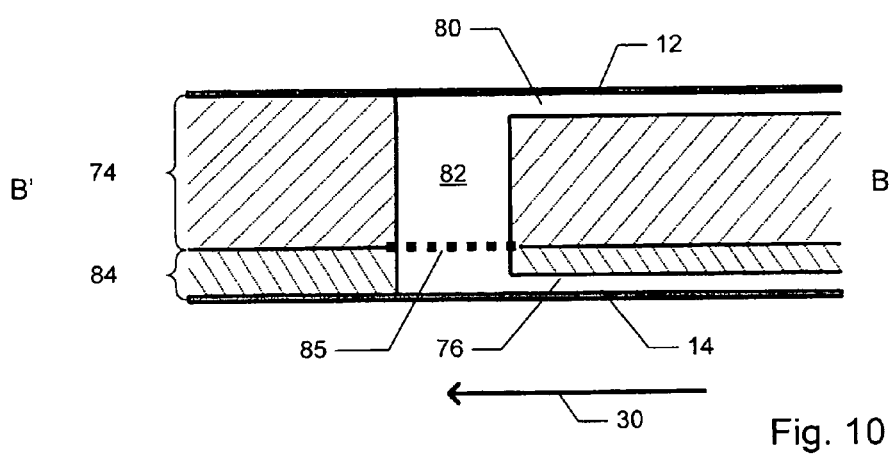
FIG. 10 is a cross-section B-B' of the marked area in FIG. 9.

A sample processing cartridge like the cartridge 10 may further comprise one or more overlying layer(s) and/or underlying layer(s) with at least one additional channel and/or cavity. In other words, the cartridge may comprise one or more systems of channels and cavities that are extending laterally in a plane parallel to previously mentioned set of channels and cavities. An example of such a cartridge is schematically illustrated in FIG. 5, and a further example is illustrated in FIGS. 8-10. The cartridge in FIG. 5 includes a level or layer 74 with various cavities and channels, including a cavity 76. The various cavities and channels in the layer 74 may for instance be the above mentioned first and second cavities, the U-shaped microchannel, etc.

In FIG. 5, the cartridge further comprises an overlying layer 78 with a cavity 80. The overlying layer 78 is placed over the layer 74. The cavity 80 in the overlying layer 78 is in fluid communication with the cavity 76 in the layer 74 by means of an inter-level channel 82. The inter-level channel 82 may extend obliquely or diagonally therebetween. By appropriately arranging the cavities 76, 80 and the inter-level channel 82 in the cartridge, fluidic matter like liquid and suspensions may efficiently be transferred via the inter-level channel 82 between the cavities 76 and 80 as the direction of a centrifugal force acting on the fluidic matter in the cartridge is changed (e.g. rotating the cartridge about the internal axis while being rotated about the external axis). In case of transporting the liquid from the lower cavity 76 up to the cavity 80, the centrifugal force of about 10×G to about 1000×G typically acting on the cartridge will be large enough to exceed the gravitation force as the liquid is moved upwards from the cavity 76 to the cavity 80.

Instead of, or as a complement to, the overlying layer(s) 78, the cartridge may include one or more underlying layer(s) 84. The underlying layer 84 may be similar to the overlying layer 78, but is located on the opposite side of the layer 74 compared to the overlying layer, as indicated in FIG. 5.

Hence, processing or testing or analysis in three dimensions may be achieved by allowing passage of the liquid or fluidic elements to the overlaying or underlying layers 78, 84. As the elements have reached an overlaying or underlying layer, the elements can by rotating the cartridge relative to the centrifugal force be processed and transferred laterally according to microchannel and cavity designs at that plane until it may be transferred back into the original plane or into a yet another plane. The liquid may be moved back and forth between multiple layers allowing increased functionalities in compact devices, i.e. without having to extend the area of the plate-shaped cartridge.

Typically absorbing material such as an absorbing pad for soaking and capture any excess of liquid or waste may be placed in a further plane of the cartridge.

Also, a filter or a porous membrane, either for filtering of particles or chemical interactions or capturing of specific molecules, may be placed at a passage from one layer to another, for instance the inter-level channel 82. This type of porous filters may be used in direct combination with the absorbing material or in conjunction with new cavities and channels extending in under-laying or overlaying layers of the cartridge. An example of such a filter or porous membrane is shown in FIG. 1a and designated 85.

Figure 6:
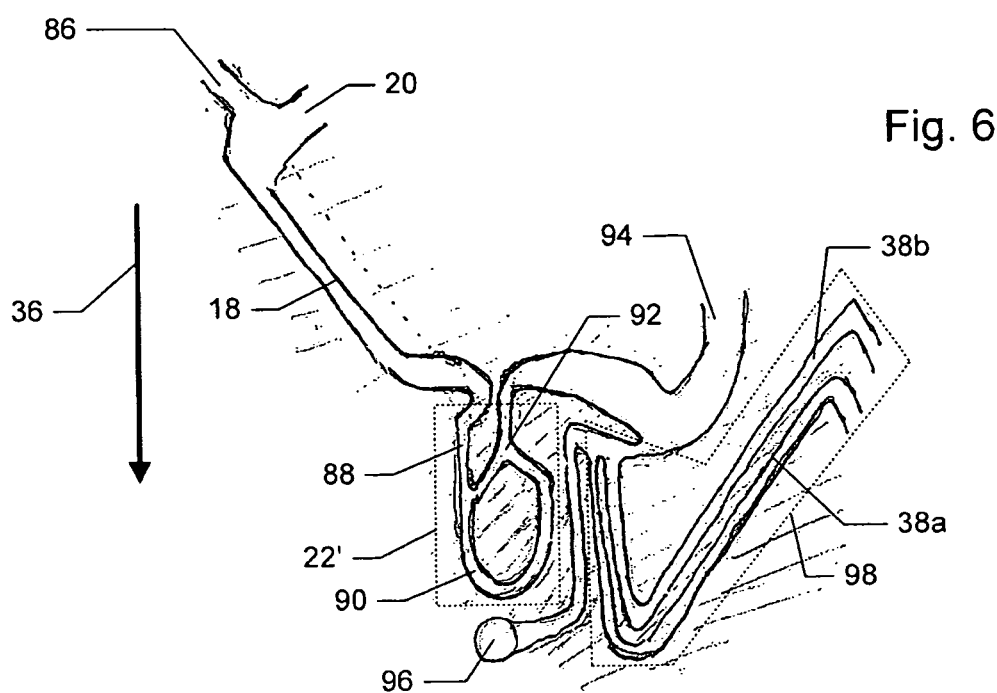
FIG. 6 is a partial top view of another sample processing cartridge according to an embodiment or embodiments of the invention.

FIG. 6 is a top view of a portion of another sample processing cartridge according to an embodiment or embodiments of the invention. The cartridge illustrated in FIG. 6 is designed for separating two defined plasma aliquots from the cells of whole blood samples in a two dimensional centrifugal system utilizing both the transfer from a deep channel extending perpendicular to the g-force (centrifugal force) to a shallow channel system extending radially in a second centrifugation position, and the design of this shallow channel system as a trap for holding higher density cells (particles) while the plasma fraction of lower density than the cells are allowed to pass. Such a process may be monitored and controlled by a camera-strobe system as disclosed in the applicant's co-pending patent application entitled "Centrifugation apparatus, use of such an apparatus, and centrifugation, and centrifugation method". The shallow channel system is further connected to a liquid splitting system allowing individual exact metering of each fraction (a and b respectively).

In particular, the cartridge of FIG. 6 comprises an inlet 20 for whole blood and a waste outlet 86 arranged at one end of the deep ("first") cavity 18. The deep cavity 18 serves to separate plasma from blood cells of a whole blood sample provided via the inlet 20, as described per se above. At the other end of the deep cavity 18, there is connected a shallow channel system 22' for trapping liquid elements (cells/particles) according to their densities. The shallow channel system 22' is overall extended in the direction of the centrifugal force 34, and is a variant of the second cavity 22 described above. The shallow channel system 22' includes an inlet channel 88 at one end in fluid communication with the deep cavity 18 and at the other end connected to a loop channel 90 of the shallow channel system 22' with an acute angle. The shallow channel system 22' further includes an outlet channel 92 also connected the loop channel 90, but in a Y-shaped connection as shown in FIG. 6.

The cartridge of FIG. 6 further comprises a second inlet 94 for an assay buffer that flushes the loop channel, securing that metered sample fractions are completely transferred from the metering loop to any subsequent reaction chamber (e.g. cuvettes, particle columns or filters), a second waste outlet 96 for plasma excess, and a system 98 for splitting and metering of isolated fractions (e.g. plasma). Said system 98 may comprise two U-shaped microchannels 38a, 38b arranged next to each other, one for each fraction a and b of the plasma. The U-shaped microchannels 38a, 38b may be formed and operated as the U-shaped microchannel 38 is described above, and thereby metering identical or different but exact liquid volumes as determined by the orientation of the cartridge relative to the centrifugal force. The split fractions of plasma may be subjected to the same reagents or different types of reagents allowing either parallel runs of the same assay, different sensitivity ranges of an analyte or different analyses.

By subsequently changing the orientation of the cartridge of FIG. 6 relative to the centrifugal force back and forth in defined steps, separation, trapping, splitting, dissolving dried reagents, mixing, and measuring of the sample or other material in the cartridge may be carried out.

Figure 7:
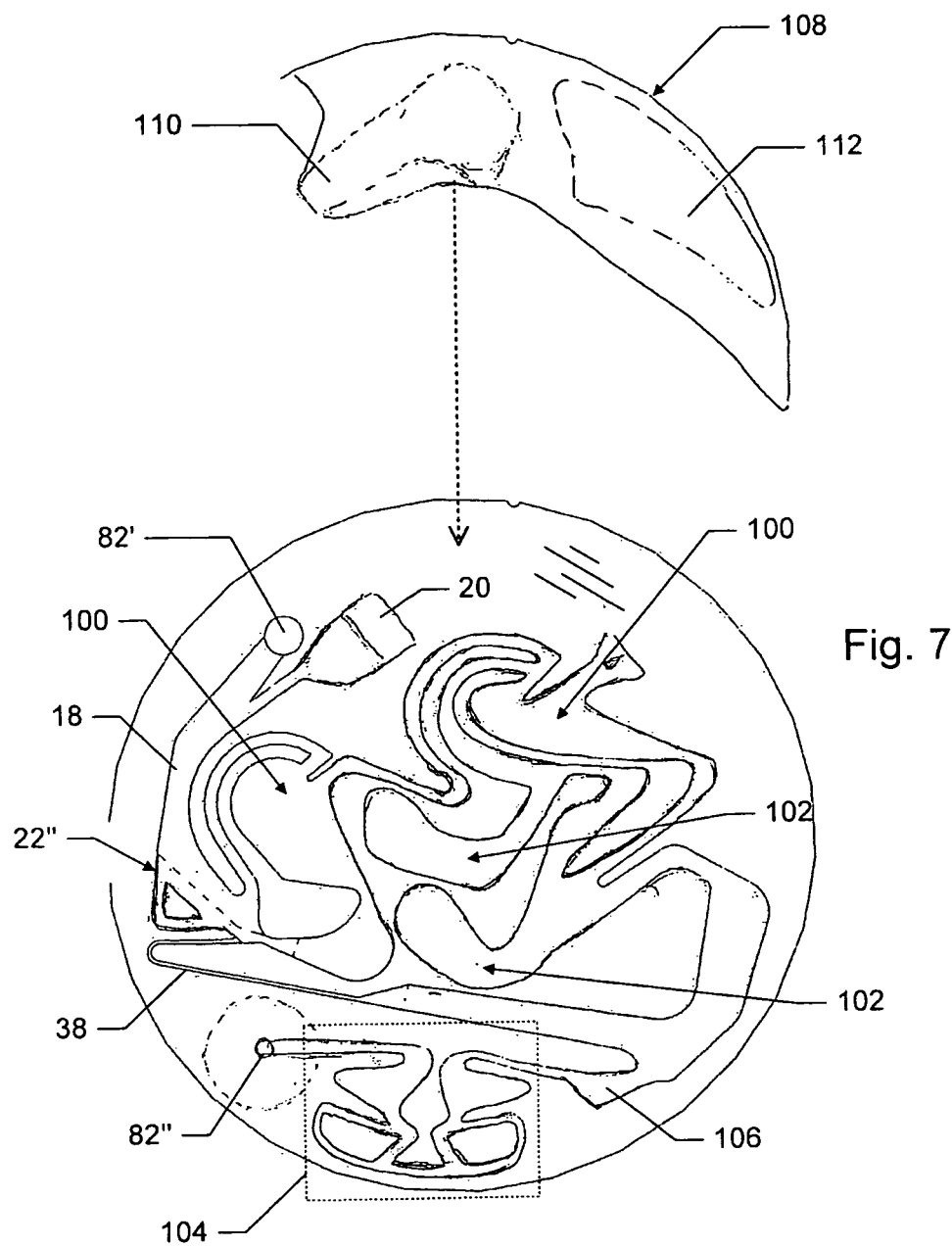
FIG. 7 is a top view of yet another sample processing cartridge according to an embodiment or embodiments of the invention.

FIG. 7 is a top view of yet another sample processing cartridge according to an embodiment or embodiments of the invention. The cartridge illustrated in FIG. 7 comprises a separation cavity for separation of e.g. plasma from blood cells of whole blood samples. The separation cavity includes a deep area 18 and a shallow area 22". The deep area 18 is similar to the first cavity 18 described above, and the shallow area 22" is a variant of the second cavity 22 described above. The separation cavity is at one end thereof in fluid communication with an inlet or cavity 20' for receiving a sample (e.g. whole blood sample) from an external sample dispending device 108 upon centrifugation. The separation cavity may at said end thereof also be in fluid communication with an opening or channel 82' allowing entrance of liquid to under- or overlying fluidic systems, as described per se above. At the opposite end of the separation cavity, it is in fluid communication with a U-shaped microchannel 38 for metering purposes, as also described per se above.

The cartridge of FIG. 7 may further comprise systems 100 of channels and cavities for splitting of a buffer, and systems 102 of channels and cavities for holding dried reagents to be dissolve and mixed with the buffer and processed according to programmed sequence, as illustrated.

Also, the cartridge of FIG. 7 may further comprise a trap 104. The trap 104 is adapted to hold higher density fluidic particles while liquid elements of lower density are allowed to pass, and it may be similar to the traps 42 and 66 in FIGS. 3a-3e and 4, respectively. One inlet of the trap 104 is through the cavity 106 connected to a channel system supplying the metered sample from U-shaped micro-channel 38 and the reagents from system 102. The other end of the trap 104 is in fluid communication with an outlet 82", typically a waste chamber or waste pad in another plane of the cartridge.

By subjecting the cartridge of FIG. 7 for a centrifugal force and then change the orientation of the cartridge relative to the centrifugal force appropriately, transportation, separation, splitting, flushing, dry reagent dissolving, mixing, trapping, washing, measuring, etc. of the sample or other material in the cartridge may be carried out sequentially and/or partly in parallel.

The sample dispending device 108 may be snapped onto the cartridge. The sample dispending device includes a cavity 110 for drawing sample (typically 10 µL whole blood as drawn from finger prick blood), and a buffer cavity 112 that is opened when the sample dispensing device 108 is attached to the cartridge.

FIGS. 8-10 illustrate yet another sample processing cartridge according to an embodiment or embodiments of the invention. The cartridge may, as illustrated in FIG. 8 and in further detail described in relation to FIGS. 9 and 10, comprise an intermediate porous material. The porous material may typically be a filter or porous membrane on which coloured, fluorimetric or other types of optically active compounds are generated through any sequence of reactions taking place as samples and reagents are flushed through the porous material. In order to view the coloured surface by an optical sensor (i.e. digital camera) placed either above or underneath the rotating cartridge, the main surface of the porous membrane should preferably be in the plane of a rotating disc (not shown) holding the cartridge. The design as illustrated in FIGS. 8-10 will allow the liquid to pass perpendicular to the centrifugal force, through the entire area of a porous membrane 85 placed parallel to the plane of the rotating disc. Liquid will under the force of centrifugation flow from a mixing cavity 106', through the (inlet) channel 80 into the inter-level channel 82. The liquid will then fill up the inter-level channel 82 before it can flow further into the (outlet) channel 76 in the underlying layer of the cartridge. Then by changing the orientation of the cartridge relative to the acting centrifugal force, the liquid will flow into the cavity 107 in the elongation of channel 76. The liquid may be flush back and forth between cavity 106' and 107 through the porous membrane 85 in the inter-level path 82 by repeated changing the orientation of the cartridge relative to the centrifugal force. Further, the liquid can be led directly to a waste cavity, typically an absorbing pad, or allowed to flow through another inter-level channel 82''' for further processing through channel 80'.

In the following, technical effects and advantages of the invention are illustrated by example of the design shown in FIG. 8. The cartridge will preferably be used in combination with a centrifuge apparatus according to the applicant's co-pending patent application entitled "Centrifugation apparatus use of such an apparatus and centrifugation method", but it may also be used in combination with an apparatus according to U.S. Pat. No. 4,814,282 (Holen et al.). In this particular example, a cartridge used to measure the amount of a specific plasma-protein (antigen) in a small blood sample based on an immunometric membrane flow through assay system is described.

The sample dispensing device 108 is used to draw a small volume of whole blood from a finger prick utilizing capillary forces of the open cavity 110. The volume of whole blood drawn is determined by the volume of cavity 110, but will usually be between 0.1 µL to 100 µL, and typically 10 µL. An exact whole blood volume may not be critical at this stage of the procedure, as the fluidic design and automated spinning and rotation of the cartridge will give exact metering of one or more plasma fractions of the sample at a later step of the automated analytical assay.

The operator will then merge the sample dispensing device 108 with the core element of the cartridge 10, these being held together by a suitable system, such as a snap lock or similar. The cartridge may hereby in a preferred situation be completely sealed, except for small hidden venting holes (not shown).

Upon this merger, the cavity 112 holding a liquid reagent will be opened for example by the cutting of a foil. The cavity 112 containing liquid reagents need not be part of the sample dispensing device, but may be placed anywhere else in the cartridge, for example in over- or underlying layers. Further, the cartridge or the sample dispensing device may hold several cavities with different liquid and/or dried reagents. After the merger of the sample dispensing device 108 and the core element of the cartridge 10, the cartridge will be place in the centrifugal apparatus by an operator of the apparatus. Except for any mechanism holding the cartridge in position in the centrifugal apparatus, there is no need for any interfaces between the cartridge and the apparatus, such as pump conjunctions, valve controllers, electrical contact plugs, or other types of interfaces. The centrifugal apparatus is designed to bring the cartridge in a defined first orientation referred to as 0 degrees on a main centrifugal plate of the centrifugal apparatus before exposing the cartridge to centrifugal forces by the spinning of this centrifugal plate.

Means within the centrifugal apparatus will typically during the initial steps read a bar code or similar on the cartridge, which barcode or similar will identify the cartridge and select the appropriate program for centrifugal spinning and cartridge rotations to be performed automatically by the apparatus in the following procedure.

Upon spinning (typically 40 Hz) the cartridge 10 being in an orientation where the centrifugal force 30=0 degrees as indicated in FIG. 8, the liquid buffer reagent of cavity 112 will by centrifugal force move into cavity 100, and further split between cavities 100, 105, and 107, while the whole blood sample will move via the inlet means 20 into the first cavity 18. The whole blood sample will due to the centrifugal force (typically 500×G) be forced to spread out in the part of cavity 18 being farthest away from the centrifugal axis. As this cavity 18 (being elongated and deep) is extended in a plane perpendicular to the centrifugal force, the blood sample will spread out in a thin layer close to the rim ("bottom") 19 of the cavity. The blood cells within the blood sample will, due to a higher density than the plasma, move to the area farthest from the centrifugal axis and occupy the area closest to the wall 19, and thereby establish a thin but distinct layer of plasma closer to axis of centrifugation. A thin layer of plasma free from blood cells is typically established within 20 to 120 seconds depending on the radius of the centrifugal plate and the speed of the centrifuge.

When the cartridge illustrated in FIG. 8 is rotated clockwise (<56 degrees) the plasma and blood cells will move in two distinct layers into the second cavity 22. In this second cavity 22, which is more extended in the direct of the centrifugal force, but shallower and narrower in the plane perpendicular to the centrifugal force than the first cavity 18, the separation of plasma from blood cells is maintained. This implies that the distance from the plasma surface to the blood cells is substantially larger than when in the previous cavity 18.

By further clockwise rotating the cartridge to 56 degrees a fraction of the cell free plasma will flow into the metering cavity 38. During this rotation the liquid reagent in the cavities 100, 105 and 107 will, due to the centrifugal force, flow respectively into cavity 102, 103 and 101. In any of these cavities the liquid reagent may dissolve dried reagents. In the particular immunometric assay as described by example, the cavity 102 will contain dried or lyophilized labelled monoclonal antibodies with specificity to the target antigen. The antibody label will typically be a strong dye such as colloidal gold, a fluorophore, an enzyme, or any other label suited for detection.

The centrifugal spinning may for the rest of the assaying be reduced to a lower speed (typically 10 Hz) than used during separation of plasma from blood cells. The cartridge of FIG. 8 is then rotated anticlockwise 83 degrees. A defined metered fraction of the plasma will be trapped in cavity 38. Excess plasma and blood cells in cavity 22 will flow through cavity 18 and the inter-level channel 82' and further into an absorption pad 87, which absorption pad may be situated on the underlying layer 84 of the cartridge. At the same time part of the liquid reagent of cavity 101 will flow into cavity 109.

The cartridge is then rotated clockwise 60 degrees allowing the liquid in cavity 109 to flow into the cavity 22 while the other liquids in the cavities 38, 101, 102 and 103 will remain within their respective cavities. Upon 60 degrees anticlockwise rotation of the cartridge, the liquid in cavity 22 will flow from this cavity into the absorption pad 87 and thereby rinse the cavities 22 and 18 for remnants of the blood sample.

Then the cartridge is rotated clockwise for 108 degrees, whereby the plasma and the liquid in cavity 101 will flow through channel 38 into the cavity 106'. The cartridge is then tilted back and forth allowing the plasma and subsequent dilution liquid to flush over the elevations within cavity 106' and thereby mixing the plasma and the dilution liquid while the liquid reagents within cavity 102 and 103 still remain within their respective cavities. The diluted plasma is then by appropriate anticlockwise rotation allowed to flow into the inter-level channel 82 containing the porous material 85, typically an antibody coated porous membrane. Upon a next clockwise rotation, the diluted plasma is forced to flush through this membrane 85 according to the previous description of FIG. 9. The immobilized antibodies on the porous membrane will specifically capture their respective antigens while all other molecules within the diluted sample will remain dissolved. Further clockwise rotation of the cartridge will make all the liquid of the diluted sample move to the underlying cavity 76 and eventually enter the inter-level channel 82'. Upon this clockwise rotation the liquid reagent containing labelled antigen specific antibodies in cavity 102 will flow into cavity 106', while the liquid in cavity 103 remain within this cavity 103. The sequence of rotations as described for flushing liquid from cavity 106' through the porous membrane 85 further into the underlying cavity 76 is then repeated. Any antigen molecule captured on the porous membrane will then bind the corresponding labelled antibody. Meanwhile the antigen depleted diluted plasma has flown through the channel 80' and the interlevel channel 82" into the absorption pad 87.

The cartridge is thereupon rotated even further in a clockwise direction making the liquid of cavity 103 to flow into cavity 106'. Then the same sequence of rotations as described for flushing liquid from cavity 106' through the porous membrane 85 further into the underlying cavity 76 is then repeated for the third time. The washing liquid will thereby remove unspecifically bound labelled antibody from the porous membrane. Eventually all the liquid reagents will end up in the absorbing pad 87.

The labelled antibody captured on the porous membrane may then be measured by optical or other means. Typically antibodies labelled with gold colloids will give rise to a red colour on the membrane, while antibodies labelled with fluorophores will emit fluorescent light upon light excitation.

Although the assay sequence described includes many steps, such a sequence of reactions may as a consequence of the invention be performed within a few minutes, typically two to five minutes.

The particular cartridge design as described in FIGS. 8-10 is an example used to demonstrate advantages of the invention as applied to the measurement of a plasma-protein by an immunometric membrane flow through assay. The invention gives added value in a variety of application areas and will function even in the outer space. A variety of samples may be used originating from any type of organic or inorganic material, virus, bacterial, fungal or eucaryote species, tissues, and body fluids. The parameters measured may be any type of inorganic, organic or biological material including low molecular weight and high molecular weight materials, proteins, lipids, nutricient, nucleic acids, cells, virus, bacteria, and so on. A variety of reagents and assay sequences including various immunochemical assay, nucleic acid extraction, purification and amplification assays, enzymatic assays and others may be performed fast and efficient by taking advantage of the invention combining modifications of the fluidic elements described in the FIGS. 1 to 10.

The person skilled in the art realized that the present invention by no means is limited to the preferred embodiments described above. On the contrary, many modifications and variations are possible within the scope of the appended claims.

Further, different features described in this application may be embodied alone or in combination, as the case may be.

To this end, it is envisaged a sample processing cartridge (for carrying out processing under centrifugal force acting in at least two directions), the cartridge comprising an overlying or underlying layer with at least one additional cavity to which the sample or material originating therefrom may be moved (but not necessarily the deeper first cavity and the shallower second cavity or any particle trap or U-shaped microchannel).

It is also contemplated a sample processing cartridge (for carrying out processing under centrifugal force acting in at least two directions), the cartridge comprising one or more substantially U-shaped micro channel(s) for metering the sample and/or reagents or material originating therefrom (but not necessarily the deeper first cavity and the shallower second cavity or any overlying/underlying layer).

It is also contemplated a sample processing cartridge (for carrying out processing under centrifugal force acting in at least two directions), the cartridge comprising at least one trap adapted to stop higher density fluidic particles but to let pass lower density fluidic particles (but not necessarily the deeper first cavity and the shallower second cavity or any overlying/underlying layer or U-shaped microchannel).

It is also contemplated a sample processing cartridge (for carrying out processing under centrifugal force acting in at least two directions), the cartridge comprising at least one unit of porous material arranged in a cavity or channel (e.g. an inter-layer channel) of the cartridge, such that other material may pass through the porous material by changing the orientation of the cartridge relative to the centrifugal force. The at least one unit of porous material may be filters, porous membranes, sensors, reactors or actuators which may carry functional groups adapted to allow extensive interaction between molecules in solution with reactive groups immobilized on the surface of the porous material.

Other aspects of the present disclosure are defined in the following clauses, represented by Roman numbers.

I. A sample processing cartridge for carrying out processing under centrifugal force in at least two directions as the orientation of the cartridge relative to centrifugal force is changed;
wherein the cartridge comprises a first cavity (18) adapted to contain a sample,
wherein the first cavity is elongated, in a plane (P) of the cartridge, perpendicular to the centrifugal force acting in a first direction of said at least two directions,
wherein the first cavity at a first end portion of its elongation is provided with a sample inlet (20),
wherein the cartridge comprises a second cavity (22) in fluid connection with a second end portion at the opposite end of the elongation of the first cavity,
wherein the first and second cavities are arranged such that the sample is moved from the first to the second cavity as centrifugal force acting on the cartridge is changed from the first direction (30) to a second direction (36) of said two directions,
wherein the second cavity is more shallow than the first cavity, and wherein the second cavity is more extended in the direction of the centrifugal force acting in the second direction than the first cavity is extended in the direction of the centrifugal force acting in the first direction.

II. A cartridge according to clause I, wherein in said plane or in a plane parallel to said plane the second cavity is less extended perpendicular to the centrifugal force acting in the second direction than the first cavity is elongated perpendicular to the centrifugal force acting in the first direction.

III. A cartridge according to any one of clauses I or II, further comprising at least one of an overlying (78) layer and an underlying (84) layer with at least one additional cavity and/or channel to which the sample or material originating therefrom may be moved.

IV. A cartridge according to any one of clauses I to III, further comprising a substantially V- or U-shaped micro channel (38) for metering the sample or material originating therefrom in fluid communication with the second cavity, but not with the first cavity.

V. A cartridge according to any of clauses I to III, further comprising at least one trap (42, 66) adapted to stop higher density fluidic particles but to let pass lower density liquids and/or fluidic particles.

VI. A cartridge according to clause V, wherein said trap includes an inlet chamber (44), an intermediate U-shaped channel (46), an outlet chamber (48), a first two-channel splitter (50) between the inlet chamber and one end of the intermediate channel, and a second two-channel splitter (54) between the opposite end of the intermediate channel and the outlet chamber.

VII. A cartridge according to clause V, wherein said trap includes a kidney-shaped loop (68) with inlet (70) and outlet (72) at the concave portion thereof.

VIII. A cartridge according to any one of clauses I to VII, wherein the first cavity is elongated in a plane of the cartridge and has a depth perpendicular to said plane, and wherein the second cavity has a smaller depth than the first cavity and extends in said plane in a different direction and by a greater amount than the width of the first cavity.

IX. A cartridge according to any one of clauses I to VIII, wherein the second cavity is configured as a channel system.

X. A cartridge according to any one of clauses I to IX, further comprising at least one porous material arranged in a cavity or channel of the cartridge, such that other material may pass through the porous material by changing the orientation of the cartridge relative to the centrifugal force.

XI. A cartridge according to any one of clauses III and X, wherein the porous material (85) is arranged in an inter-level channel (82) to the overlying layer and/or an underlying layer.

XII. A cartridge according to clause XI, wherein an inlet (80) to the inter-level channel (82) is provided at one end of the inter-level channel (82) in one layer (74) of the cartridge, the inlet being arranged in substantially the same direction as an outlet (76) from the inter-level channel (82), which outlet is provided at the other end of the inter-level channel (82) in another layer (84) of the cartridge.

The invention claimed is:

1. A method of processing and/or analyzing a sample under centrifugal force, the method comprising:
providing a sample processing cartridge having a first elongated separation cavity adapted to contain the sample and a second cavity in fluid communication with the first elongated separation cavity, the first elongated cavity having a curvature shape extending in a longitudinal direction thereof;
providing the sample in the first elongated separation cavity of the sample processing cartridge;
subjecting the cartridge to a centrifugal force acting in a first direction, wherein the longitudinal direction of the first elongated separation cavity extends in a plane of the cartridge, perpendicular to the centrifugal force acting in the first direction; and
changing the centrifugal force from the first direction to a second direction such that the sample in the first elongated separation cavity is moved therefrom to the second cavity,
wherein the second cavity is shallower than the first elongated separation cavity and more extended in the direction of the centrifugal force acting in the second direction than the first elongated separation cavity is extended in the direction of the centrifugal force acting in the first direction,
wherein the cartridge is subjected to the centrifugal force by rotating the cartridge about an external axis, and wherein the direction of the centrifugal force is changed by rotating the cartridge about an axis within the cartridge.

2. A method according to claim 1, further comprising allowing the sample, or material originating from said sample, to enter a second system of channels and cavities that are extending laterally in a plane of the cartridge, said plane being parallel to a first system of channels and cavities, the first system including the first elongated separation cavity and the second cavity.

3. A method according to claim 1, wherein the sample processing cartridge further comprises a V- or U-shaped micro channel for metering the sample, or material originating from said sample, and wherein the method further comprises:
subjecting the cartridge to a centrifugal force exceeding the capillary force of the V- or U-shaped micro channel.

4. A method according to claim 1, wherein the sample processing cartridge further comprises at least one trap adapted to stop higher density fluidic particles but to let pass lower density liquids and/or fluidic particles.

5. A method according to claim 4, wherein said trap includes: an inlet chamber, an intermediate U-shaped channel, an outlet chamber, a first two-channel splitter between the inlet chamber and one end of the intermediate channel, and a second two-channel splitter between the opposite end of the intermediate channel and the outlet chamber.

6. A method according to claim 4, wherein said trap includes a kidney-shaped loop with inlet and outlet at the concave portion thereof.

7. A method according to claim 1, wherein the longitudinal direction of the first elongated separation cavity extends in a plane of the cartridge, and the first elongated separation cavity has a depth perpendicular to said plane, and wherein the second cavity has a smaller depth perpendicular to said plane than the first elongated separation cavity and extends in said plane in a different direction and by a greater amount than the width of the first cavity.

8. A method according to claim 1, wherein the second cavity is configured as a channel system.

9. A method according to claim 1, wherein the sample processing cartridge further comprises at least one porous material arranged in a cavity or channel of the cartridge, and where in the method further comprises:

changing the orientation of the cartridge relative to the centrifugal force such that a material originating from the sample passes through the porous material.

10. A method according to claim 2, wherein a porous material is arranged in an inter-level channel between the first system and the second system.

11. A method according to claim 10, wherein an inlet to the inter-level channel is provided at one end of the inter-level channel in the first or second system of the cartridge, the inlet being arranged in the same direction as an outlet from the inter-level channel, which outlet is provided at the other end of the inter-level channel in the first or second system of the cartridge.

12. A method according to claim 9, wherein a porous material is arranged in an inter-level channel between the first system and the second system.

* * * * *